Figure 1:
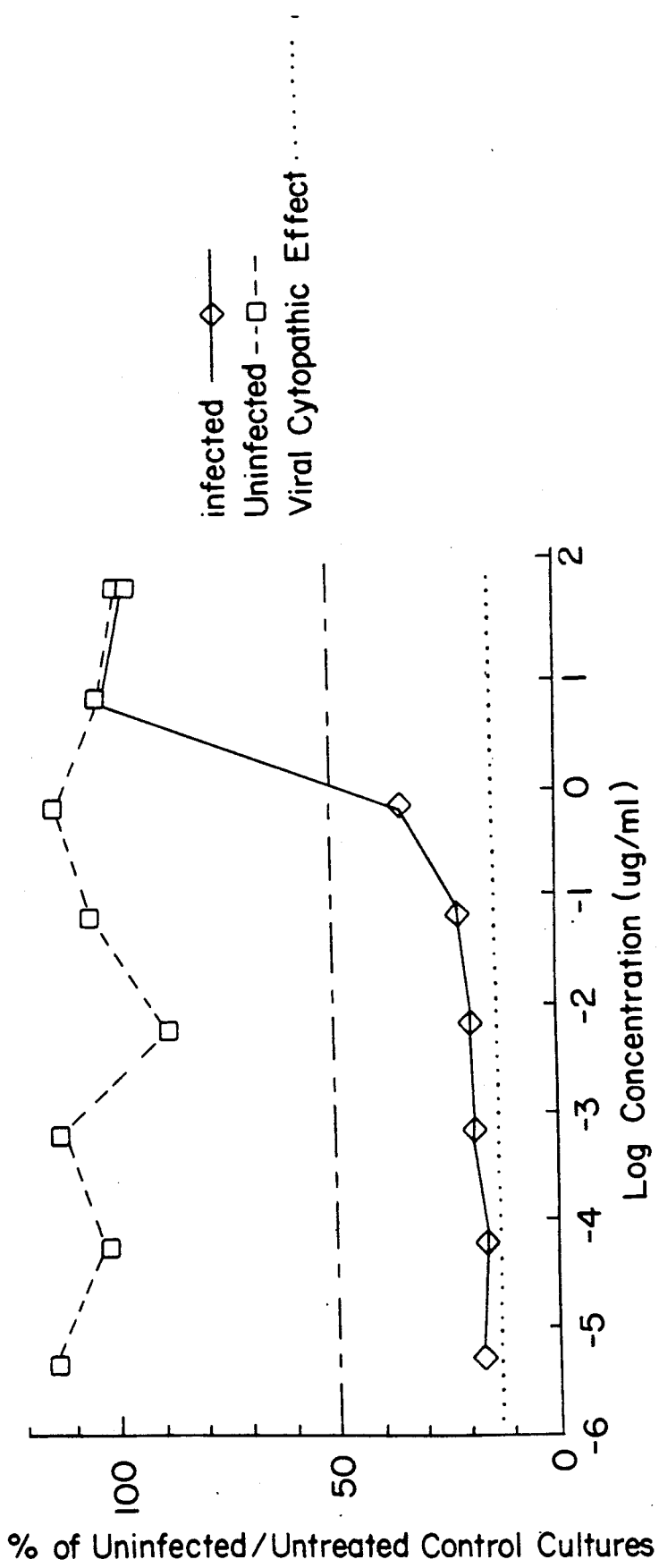

United States Patent [19]

Kalman

[11] Patent Number: 5,051,498

[45] Date of Patent: Sep. 24, 1991

[54] LIPOPHILIC 2', 3'-DIDEOXYNUCLEOSIDE PRODRUG DERIVATIVES FOR THE INHIBITION OF REPLICATION OF THE AIDS VIRUS AND OTHER RETROVIRUSES

[75] Inventor: Thomas I. Kalman, East Amherst, N.Y.

[73] Assignee: The Research Foundation of State University of NY, Albany, N.Y.

[21] Appl. No.: 431,286

[22] Filed: Nov. 3, 1989

[51] Int. Cl.$^5$ .............................................. C07H 19/00
[52] U.S. Cl. ........................................ 536/23; 536/26
[58] Field of Search ...................... 536/23, 26; 514/49, 514/50

[56] References Cited

U.S. PATENT DOCUMENTS 3,817,982  6/1974  Verheyden et al. .................. 536/23

FOREIGN PATENT DOCUMENTS 1811267  1/1968  Fed. Rep. of Germany .
2065281  11/1975  Japan ..................................... 536/23
3141284  5/1977  Japan ..................................... 536/23

OTHER PUBLICATIONS

Yarchoan et al., New England Journal of Medicine, v 316: 557–564.
Chem. Abst.: vol. 71(13), 61706x, Holy et al. (1969).
Journal of Med. Chem, vol. 30, p. 2131 (1987).
J. Zemlicka, Collection Czechoslov. Chem. Commun., NOTES, vol. 28, 1963, pp. 1060–1062.
J. Zemlicka et al, Collection Czechoslov. Chem. Commun., vol. 32, 1967, pp. 3159–3168.
A. Holy et al, Collection Czechoslov. Chem. Commun., vol. 34, 1969, pp. 2449–2458.
J. A. Oates et al, New England J. of Medicine, vol. 321, No. 11, Sep. 14, 1989, pp. 726–738.
Chong-Ho Kim et al, J. Med. Chemistry, vol. 30, 1987, p. 862.
S. Hanessian, J. Med. Chemistry, vol. 16, No. 3, 1973, pp. 290–292.

*Primary Examiner*—John W. Rollins
*Assistant Examiner*—James O. Wilson
*Attorney, Agent, or Firm*—Howard M. Ellis; Michael L. Dunn

[57] ABSTRACT

The invention provides new alkylaminomethylene 2',3'-dideoxynucleoside compounds and salts thereof.

7 Claims, 4 Drawing Sheets

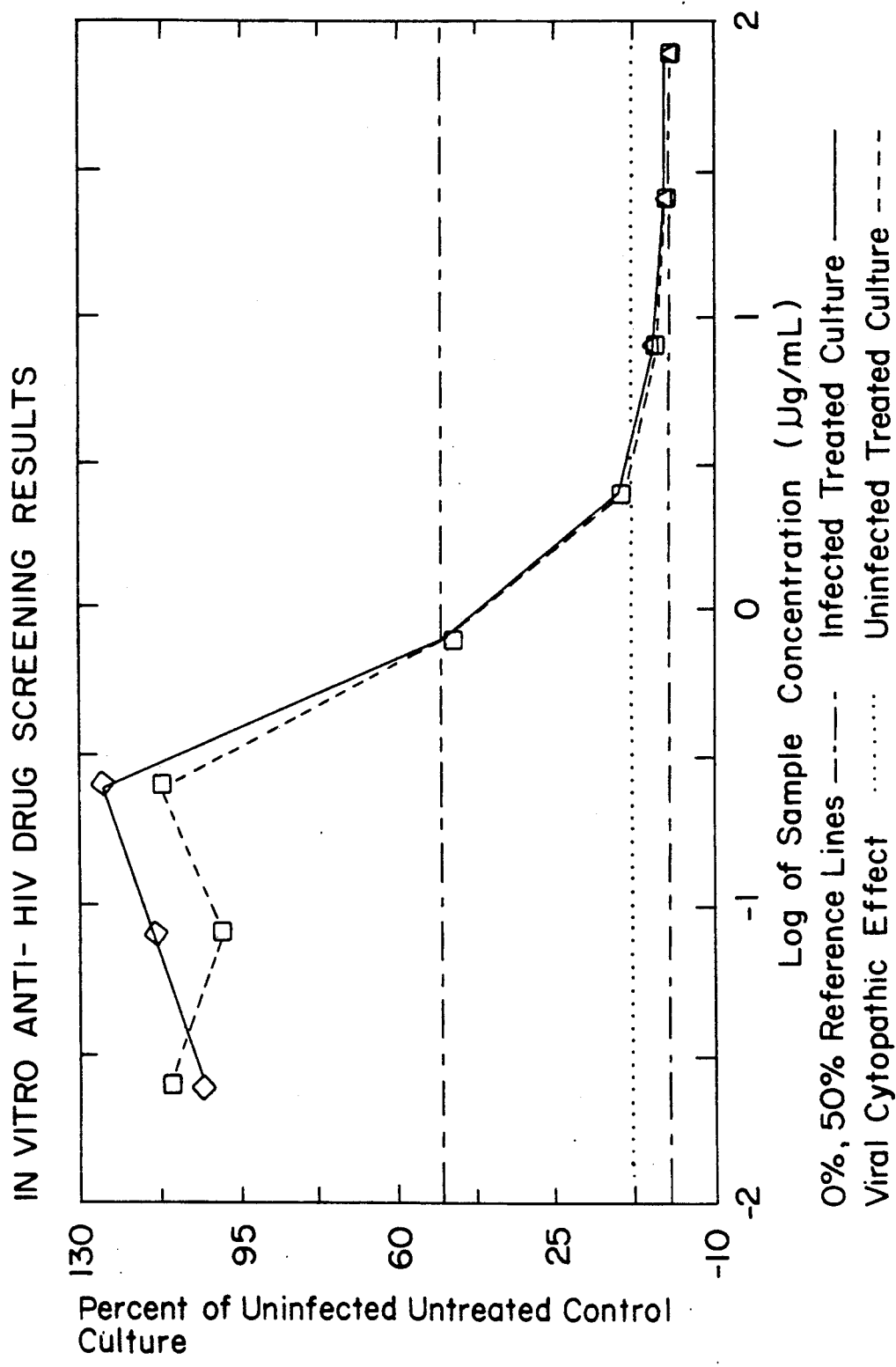

LIPOPHILIC 2′, 3′-DIDEOXYNUCLEOSIDE PRODRUG DERIVATIVES FOR THE INHIBITION OF REPLICATION OF THE AIDS VIRUS AND OTHER RETROVIRUSES

BACKGROUND OF THE INVENTION

This invention was made in with part government support under Grant Number 1RO1AI2725-O1A1 awarded by the National Institutes of Health, Department of Health and Human Services. The government has certain rights in this invention.

Since the first cases of acquired immunodeficiency syndrome (AIDS) were recognized in 1981, this fatal disease has claimed thousands of lives and reached epidemic proportions. By the end of 1987 in the USA alone, more than 28,000 people died of AIDS. AIDS is caused by a retrovirus, human immunodeficiency virus (HIV), previously referred to as human T-cell lymphotropic virus type III/lymphoadenopathy-associated virus (HTLV-III/LAV). Infection by HIV results in severe immunosuppression characterized by a progressive loss of helper T4+ lymphocytes which are killed by the virus when it replicates. AIDS patients lacking an effective host-defense mechanism which depends on T4+ cells, succumb to severe opportunistic infections and/or malignant tumors. Serious neuropathies also complicate the clinical picture of the disease, primarily as a consequence of the invasion of the central nervous system by HIV.

HIV belongs to the Retroviridae family and resembles the type-D retroviruses of the Lentivirinae subfamily. Thus, it is more closely related to the animal lentiviruses, e.g., visna virus, than to the transforming human T-cell leukemia viruses HTLV-I and HTLV-II, which do not have a cytopathic effect. The virion is an enveloped sphere-shaped particle of 100–140 nm diameter with a condensed cylindrical core, which contains its 9.5 kb single stranded RNA genome together with several copies of the enzyme reverse transcriptase.

Infection of a cell by HIV requires the presence of a membrane receptor (CD4), which can recognize and bind the viral glycoprotein gp120. It should be noted that in addition to T4 lymphocytes, other cells, including the monocytes and macrophages, the predominant cell types infected by HIV in the brain, also express the CD4 receptor on their surface. Following binding, the virus enters the cells, becomes uncoated and the genomic RNA is transcribed into DNA by the viral reverse transcriptase. The RNA of the resulting RNA DNA hybrid is then digested, the DNA replicated and circularized to double stranded proviral DNA. Some of the DNA is integrated into chromosomes of the host cell, where it remains in a latent state until the infected cell becomes activated. In the activated cell the proviral DNA is transcribed into viral RNA, which is processed to functional messenger and translated into viral proteins, which subsequently become glycosylated. The genomic RNA and the viral proteins are assembled and the mature HIV particles are released by budding through the cell membrane containing the viral glycoproteins.

The HIV replication cycle offers many potential targets for drug action, e.g., receptor binding, penetration, and uncoating of the virus, reverse transcription of viral RNA, circularization and integration of proviral DNA, transcription, processing and translation of viral mRNA, processing of viral proteins, virion assembly and budding, as well as various components of the viral genetic regulatory network. The search for agents capable of selectivity hitting any of these targets is being actively pursued in many laboratories. Presently, Zidovudine (Retrovir, azidothymidine, AZT) remains the sole anti-AIDS drug on the market. In addition, several other agents have received IND approval and entered clinical trials. There are many agents effective against HIV in vitro acting by different mechanisms, and rapid development of these drug candidates is under way.

An important group of anti-HIV agents are the 2′,3′-dideoxynucleosides, which after intracellular phosphorylation to their 5′-triphosphates and incorporation into the newly synthesized viral DNA by reverse transcriptase act as chain-terminators, due to the lack of the 3′-OH group essential for phosphodiester bond formation. They inhibit viral reverse transcriptase much more strongly than cellular DNA polymerase α. AZT, the 3′-azido derivative of thymidine, is believed to exert its anti HIV activity through this mechanism. Clinical experience with AZT is growing. The drug does not cure AIDS, but provides considerable therapeutic benefit to patients with AIDS or AIDS related complex (ARC). Its major drawback is severe bone marrow toxicity, leading to anemia, leukopenia and neutropenia. Although AZT is orally effective, it has a short half-life and must be taken continuously every 4 hours at a dose of 250 mg or more. It is expensive: the annual cost for one patient is $7,000–$10,000. Two other analogs, 2′,3′-dideoxycytidine (ddC) and 2′,3′-dideoxyadenosine, are promising drug candidates of this group of agents. Phase I and II trials with ddC revealed much less bone marrow suppression with this agent, however, peripheral neuropathy poses special problems and it is the dose limiting toxicity of this drug. Recently, AIDS patients were given weekly alternating regimen of AZT and ddC with encouraging results. Since the two drugs have different toxicity profiles, this mode of administration may permit adequate recovery from toxicity without compromising anti-viral activity in some patients. Other combination modalities of AZT and ddC are in clinical trials.

The currently available nucleoside analogs exhibit many recognized shortcomings including short plasma half-life, insufficient penetration into the CNS, low therapeutic index, low potential for metabolic activation and/or high susceptibility to catabolism, and the emergence of clinical resistance. Thus there is a continuing demand for more effective antiviral agents for use in the treatment of AIDS and related viral infections. In attempts to overcome these difficulties, a variety of prodrugs of antiviral agents have been synthesized and examined for therapeutic values.

For purposes of this specification the term "prodrug" is defined as a derivative of the active form of a known composition which derivative, when administered to a mammal is gradually converted to the active form to produce a better therapeutic response and/or a reduced toxicity level.

The term "transient" will be used to describe the action of the time-dependent release of the active form of a composition from its prodrug derivative by chemical hydrolysis or other means including but not limited to enzymatic action, in such a manner that the active form is released from the derivative and the residue which remains of the derivative is essentially nontoxic and/or is metabolized to nontoxic metabolic by-products.

An object of this invention is to provide new, transient lipophilic 2',3'-dideoxynucleoside prodrug derivatives useful in the chemotherapy of AIDS which exhibit prolonged duration of action and decreased cellular and systemic toxicities.

A further object of this invention is to provide new lipophilic 2',3'-dideoxynucleoside prodrug derivatives demonstrating an increased ability to cross biological membranes, particularly the "blood brain barrier."

A still further object of the invention is to provide new 2',3'-dideoxynucleoside prodrug derivatives demonstrating varying degrees of lipophilicity and susceptibility to hydrolysis, permitting the optimization of pharmacokinetic properties and therapeutic effectiveness.

A still further object of the invention to provide a compound suitable as a topical in vitro disinfectant for AIDS virus.

These and other objects of this invention will become apparent from the following description of the invention.

DESCRIPTION OF THE INVENTION

This invention relates to new lipophilic prodrug forms of 2', 3'-dideoxynucleoside derivatives; to compositions comprising these derivatives, and to methods of using these derivatives in the treatment of AIDS.

In accordance with this invention, new alkylaminomethylene-2',3'-dideoxynucleoside prodrugs are provided having the formula

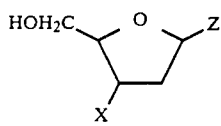

wherein X is hydrogen or fluorine and wherein Z is a pyrimidin-1-yl or a purin-9-yl selected from the group consisting of cytosine, adenine and guanine, wherein divalently attached to the exocylic amino group on said base is a substituted methylene group having the formula

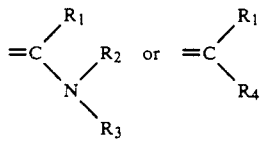

wherein $R_1$ may be selected from the group consisting of hydrogen or a $C_1$-$C_{20}$, linear or branched chain, alkyl, alkenyl or alkynyl group and wherein $R_2$ and $R_3$ may be the same or different and may each be selected from the group consisting of a $C_1$-$C_{20}$, linear or branched chain, alkyl, alkenyl or alkynyl group, or alternatively a $C_3$-$C_6$ cycloalkyl group or an aralkyl group and wherein $R_4$ may be selected from the group consisting of pyrrolidines, piperidines, or morpholines having the nitrogen divalently attached to the methylene group, and pharmaceutically acceptable salts thereof.

Further, in accord with the invention, new compositions, particularly disinfectants and pharmaceutical compositions, are provided which contain the compounds of the invention.

In addition, a method for treating acquired immunodeficiency syndrome is provided wherein one or more of the afore-described compounds is administered to a mammal.

An example of a suitable pyrimidine base is cytosine. Examples of suitable purine bases include adenine and guanine.

The sugar moiety, preferably selected from 2,3-dideoxy-D-ribofuranose or 2,3-dideoxy-3-fluoro-D-ribofuranose is covalently bonded in β-linkage via its $C_1$ to the $N_1$ or $N_9$ at the pyrimidine or purine base, respectively, to form the corresponding nucleoside.

Within the description of the compounds of the invention, particularly the designation $R_1$, $R_2$ and $R_3$ by the term alkyl, alkenyl and alkynyl is meant alkane, alkene and alkyne hydrocarbon substituents having from 1 to about 20 carbon atoms. Substituents can be straight chained, or branched and include isomers thereof. Thus the term alkyl includes methyl, ethyl, n-propyl, i-propyl, n-butyl, i-butyl, t-butyl, pentyl, hexyl, heptyl and the like up to about 20 carbon atoms. Similarly, the term alkenyl includes unsaturated hydrocarbons having one or more double bonds therein such as ethene, propene, butene, pentene and the like up to about 20 carbon atoms. Also similarly the term alkynyl includes hydrocarbons having one or more triple bonds therein such as acetylene, methyl acetylene, ethyl acetylene and the like up to about 20 carbon atoms. In addition, aralkyl is meant an aromatic ring linked through one or more methylene groups. Thus, the known aralkyl includes benzyl, phenylethyl and the like upto about 20 carbon atoms.

$R_4$ may be selected from substituted or unsubstituted pyrrolidines, piperidines or morpholines. Typical such compounds include the following: $N^4$-2-methylpiperidinomethylene-2',3'-dideoxycytidine, $N^4$-2-methylpiperidinomethylene-2',3'-dideoxy-3'-fluorocytidine.

$R_1$, $R_2$, $R_3$ and $R_4$ are preferably attached to the exocyclic amino group present on the pyrimidine or purine base through a substituted methylene linking group forming a series of side chain-bearing nucleoside derivatives. It has been discovered that the introduction of dialkylaminomethylene substituents at the $NH_2$-group of the parent dideoxynucleosides with anti-HIV activity leads to a series of nitrogen substituted prodrugs exhibiting decreased toxicity and selectively enhanced lipophilicities favorable for efficient penetration into the central nervous system.

Typical dialkylamino substituted nucleoside derivatives falling within the structure of the claimed invention include: $N^4$-dimethylaminomethylene-2',3'-dideoxy-3'-fluorocytidine (DDFC); $N^4$-diethylaminomethylene-2',3'-dideoxy-3'-fluorocytidine; $N^4$-diisopropylaminomethylene-2',3'-dideoxy-3'-fluorocytidine; $N^4$-di-n-butylaminomethylene-2',3'-dideoxy-3'-fluorocytidine (wherein "n" is normal); $N^4$-morpholinomethylene-2',3'-dideoxy-3'-fluorocytidine; $N^4$-pyrrolidinomethylene-2',3'-dideoxy-3'-fluorocytidine; $N^4$-piperidinomethylene-2',3'-dideoxy-3'-fluorocytidine; $N^4$-2,6-dimethylpiperidinomethylene-2',3'-dideoxy-3'-fluorocytidine; $N^4$-dimethylaminomethylene-2',3'-dideoxycytidine; $N^4$-diethylaminomethylene-2',3'-dideoxycytidine; $N^4$-diisopropylaminomethylene-2',3'-dideoxycytidine; $N^4$-di-n-butylaminomethylene-2',3'-dideoxycytidine (wherein "n" is normal); $N^4$-morpholinomethylene-2',3'-dideoxycytidine; $N^4$-pyrrolidinomethylene-2',3'-dideoxycytidine; $N^4$-piperidinomethylene-2',3'-dideoxycytidine; $N^4$-2,6-dimethylpiperidinomethylene-2',3'-dideoxycytidine; $N^6$-dimethylaminomethylene-2',3'-dideoxyadenosine; $N^6$-diisopropylaminomethylene-2',3'-dideoxyadenosine and the like.

Generally, the preparation of the 2',3'-dideoxynucleosides and 2',3'-dideoxy-3'-fluoronucleosides of the invention can be attained through many known routes. For example, 2',3'-dideoxycytidine (ddC) may be prepared according to the method of Prisbe and Martin as described in Synth. Commun. 15, 401 (1985) the disclosure of which is incorporated by reference herein. Briefly, this method involves the conversion of N, 5'-dipivaloyl-2'-deoxycytidine obtained by treatment of 2'-deoxycytidine with pivaloyl chloride, to its 3'-thionocarbonate using N,N'-thiocarbonyldiimidazole in DMF at 80° C. Subsequent reduction using tri-n-butyltin hydride followed by ammonolytic deprotection leads to the product. An alternative synthetic method is also available starting with 2',3'-dideoxyuridine, and involves ammonolysis of the intermediate acetylated 4-triazolylpyrimidinone derivative. [Lin et al., J. Med. Chem. 30, 440 (1987).]

Method for the preparation of 2',3'-dideoxy-3'-fluorocytidine from 5'-trityl-2'-deoxycytidine using the fluorinating reagent DAST was recently described by Herdewijn et al., J. Med. Chem. 30, 1270 (1987), the disclosure of which is hereby incorporated by references herein.

The general procedure for preparation of the dialkylaminomethylene cytosine nucleosides modified at the exocyclic amino group on the pyrimidine base involves reacting one equivalent of the nucleoside with an excess of the dialkylformamide dimethylacetal in dry DMF (or dimethylacetamide, DMSO or a similar polar solvent) in the absence of moisture. [Zemlicka et al., Coll. Czech. Chem. Commun. 32, 3159 (1967).] The contents are allowed to stir overnight and then the solvent and excess reagent are removed by rotary evaporation. The syrupy residue obtained is then subjected to crystallization typically from ethanol or ethanol-ether mixture to obtain the desired nucleoside.

In a typical reaction—previously dried 2',3'-dideoxycytidine (153 mg, 0.724 mmoles) prepared by the literature procedures described above is treated with diisopropylformamide dimethylacetal (1.27 g, 7.24 mmoles) in anhydrous DMF (2 mL) under an argon atmosphere. The contents are stirred overnight and then the solvent and excess reagent are removed by rotary evaporation. The syrupy residue remaining is crystallized from ethanol-ether to give pale lemon-colored crystals (185 mg, 79%) of diisopropylaminomethylene 2',3'-dideoxycytidine.

If the dimethylacetal starting material is unavailable, it may be prepared by reacting one equivalent of the appropriate formamide with an equivalent of dimethylsulfate at 85° C. for 60 hours to form the dialkylformamide dimethylsulfate adduct. This adduct is next treated dropwise with an equivalent of sodium methoxide in methanol at −5 degrees–0 degrees Celsius for a period of 4–5 hours. The contents are then distilled under vacuum to obtain the desired acetal. [Bredereck et al., Chem. Ber. 101, 41 (1968).]

In a typical reaction—Diisopropylformamide (50 g, 0.386 moles) is treated with dimethylsulfate (48.76 g, 0.386 moles). The contents are stirred at 85° C. for 60 hours to form the adduct. Next a solution of sodium methoxide (8.87 g, 0.386 moles of sodium in 138 mL of anhydrous methanol) added dropwise over a period of 4–5 hours maintaining the temperature at −5° C. Next, the excess methanol is removed by rotary evaporation under an argon atmosphere and the remaining contents are vacuum distilled under an argon atmosphere to give 38 g (60%) of the diisopropylformamide dimethylacetal.

As is well recognized by those skilled in the art pertaining to the instant invention, any number of systematic variations in the structure of the methylene substituted exocyclic amino side chain may be introduced using known methods similar to those set forth above. By altering the nature of the dialkyl substituent in the terminal N-atom of the side chain with an appropriate substituent a wide variety of prodrugs can be attained exhibiting increasing or decreasing variations in their lipophilicity, permitting the selection of that degree of lipophilicity which is optimal for enhancing the drug's ability to cross a particular biological membrane and the intended site of action for the drug. The systematic variation of different substituents allow the optimization of pharmacokinetic parameters leading to the enhancement of therapeutic effectiveness.

The nucleosides of the present invention can be converted into the acid addition salts via reaction with acid, both organic and inorganic, such as aliphatic, alicyclic, araliphatic, aromatic and heterocyclic mono- and polybasic acids, sulfonic acids, and the well known mineral acids. Exemplary of suitable, physiologically acceptable salt forming acids are aliphatic, alicyclic, araliphatic, aromatic, heterocyclic, mono-and polybasic carboxylic and sulfonic acids, exemplary of which are formic, acetic, propionic, pivalic, diethylacetic, oxalic, malonic, succinic, maleic, lactic, tartaric, malic, aminocarboxylic, sulfamic, benzoic, salicylic, phenylpropionic, citric, gluconic, ascorbic, nicotinic, isonicotinic methanesulfonic, p-toluene-sulfonic, sulfuric, nitric, hydrohalic, phosphoric acids and the like.

The transient prodrug compounds of this invention are useful as inhibitors of viruses and retroviruses, and particularly, as inhibitors of the AIDS HIV retrovirus. Once administered, the methylene substituted side chain undergoes spontaneous hydrolysis at physiologic pH leading to a sustained release of the parent nucleoside analog.

The compounds of this invention can be used in oral, injection and perfusion treatment of AIDS in substantially the same manner as prior known anti-AIDS derived compounds.

The compounds of this invention can be used in admixture with pharmaceutically acceptable organic or inorganic carriers suitable for parenteral, external or topical applications, it being understood that carriers suitable for use with the present compounds will not react in a deleterious manner with the compounds. Suitable, pharmaceutically acceptable carriers include, but are not limited to, water, salt solutions, alcohols, vegetable oils, polyethylene glycols, gelatin, lactose, amylose, magnesium stearate, talc, silicic acid, paraffins, perfume oils, fatty acid mono and diglycerides, hydroxy alkylcelluloses, polyvinyl pyrrolidone and the like.

The pharmaceutical preparations may also optionally include auxiliary agents such as lubricants, preservatives, stabilizers, wetting agents, emulsifiers, buffers, salts for influence of osmotic pressure, flavoring, coloring and like substances which are nonreactive with the active compounds.

For parenteral application, particularly useful are oily or aqueous sonicated solutions as well as suspensions and emulsions.

Enteric application can be realized by compounding the compounds as tablets, capsules with carriers and binders of talc, carbohydrate or the like. Sustained release properties may be included by the utilization of differentially degradable coatings such as microencapsulation, multiple coatings or the like.

As topical applications, the compounds are employed in compositions having consistencies ranging from viscous to solid non-sprayable utilizing pharmaceutically acceptable carriers commonly used in topical applications. Suitable formulations include but are not limited to solutions, suspensions, creams, ointments, emulsions, powders, liniments, salves and the like which may include such axiliary agents as preservatives, stabilizers, wetting agents, buffers and the like.

Sprayable aerosol formulations incorporating the active compounds of this invention are also within the purview of topical application, the active compound preferably in combination with a solid or liquid inert carrier packaged in a suitable dispensing container, pressurized by means of a volatile, normally gaseous propellant, such as freon and the like.

In topical formulations, the active compounds of this invention are utilized at concentrations of from about 5 to about 10 percent by weight.

The novel compounds of the present invention are generally administered to mammals, including but not limited to man in an AIDS retroviral inhibiting effective daily dosage of the active compound from about 1 mg/kg animal body weight to about 500 mg/kg animal body weight of the organism being treated. In general, large animals require less of any pharmaceutical compound per kilogram of body weight than smaller animals. The dosage amount may be administered in multiple daily dosages.

Generally, the dosage in man is lower than for small warm blooded mammals such as mice. A dosage unit may comprise a single compound of the invention or mixtures thereof with other compounds of the invention, or other compounds useful in the treatment of AIDS.

It is to be appreciated that the actual preferred and effective amounts of the compounds of this invention used will vary according to the specific compound being utilized, the particular compositions formulated, the application mode, as well as the particular sites and organism being subjected to treatment. Factors which generally tend to modify drug action will be taken into consideration by those of skill in the art, such factors as age, weight, sex, diet, times and methods of administration, reaction sensitivities, severity of the condition treated, etc. Optimal application rates for any given set of conditions can be determined by those skilled in the art employing conventional dosage determination tests, considering the foregoing guidelines.

The following specific embodiments are set forth to illustrate the preparation and use of the compounds of the present invention and are not to be construed as limitative. Unless otherwise indicated, all parts and percentages are by weight.

EXAMPLE 1

Synthesis of $N^4$-dimethylaminomethylene-2',3'-dideoxy-3'-fluorocytidine.

Previously dried 2',3'-dideoxy-3'-fluorocytidine (300 mg, 1.3 mmoles) was treated with dimethylformamide dimethylacetal (0.45 g, 3.8 mmoles) in anhydrous DMF (5 mL) under a nitrogen atmosphere. The contents were stirred overnight and the solvents removed by rotary evaporation. The syrupy residue remaining was crystallized from ethanol to give white crystals (276 mg, 75%) of the product $N^4$-dimethylaminomethylene-2',3'-dideoxy-3'-fluorocytidine which were shown to have the following properties:

| | | |
|---|---|---|
| Melting Point: | 203° C. | |
| Elemental Analysis: | $C_{12}H_{17}FN_4O_3$ (284.30). | |
| | Calcd | Found |
| C | 50.70 | 50.68 |
| H | 6.03 | 6.05 |
| N | 19.70 | 19.68 |
| Infrared and $H^1$NMR Spectra: | Consistent with the structure. | |
| Ultraviolet Spectra | | |
| In Ethanol: | $\lambda_{max}$ 317 nm, $\epsilon$36,200 | |
| | $\lambda_{min}$ 242 nm, $\epsilon$2,040 | |
| Optical Rotation: | $[\alpha]_D^{25}$ + | |
| | 130.5° (c = 1.00, EtOH) | |

EXAMPLE 2

A comparison of retention times obtained by reverse phase high pressure liquid chromatography (HPLC) resulting from various substitutions at the $N^4$-position dialkylaminomethylene side chain is set forth below. Based on economic considerations 2'-deoxycytidine, was used as the parent nucleoside for comparison purposes in this study. The results shown in Table 1 revealed marked increase in lipophilicity in the series 1-9, as reflected by the increase in retention time.

The rates of hydrolysis of the different derivatives depend greatly on the structure of the substituent introduced at the exocyclic $NH_2$-group. For example, the half-life ($t_{\frac{1}{2}}$) of $N^4$-dimethylaminomethylene 2'-deoxycytidine (compound 3 in Table 1) is 5 hours at 37° in 10 mM K-phosphate buffer at pH 7.4, as determined by UV spectroscopy and HPLC analysis. Under the same conditions, $N^4$-diisopropylaminomethylene 2'-deoxycytidine (compound 7 in Table 1) has a $t_{\frac{1}{2}}=3$ days. Thus, there is a 15-fold difference in the rate of hydrolysis of these two side chains. The variations in the susceptibility to hydrolysis provide another parameter for the optimization of the pharmacokinetic profile.

TABLE 1

General Structure:

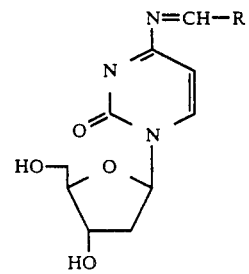

| Compound | R | Retention Time (min) |
|---|---|---|
| 1. 2'-Deoxycytidine | — | 2.13 |

TABLE 1-continued

General Structure:

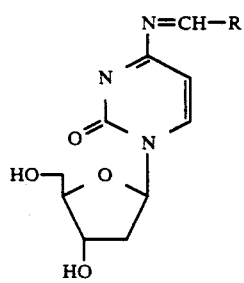

| Compound | R | Retention Time (min) |
|---|---|---|
| 2. N⁴-Morpholinomethylene-2'-deoxycytidine | —N⟨O⟩ (morpholino) | 3.07 |
| 3. N⁴-dimethylaminomethylene-2'-deoxycytidine | $-N(CH_3)_2$ | 3.26 |
| 4. N⁴-Pyrrolidinomethylene-2'-deoxycytidine | —N⟨ ⟩ (pyrrolidino) | 5.16 |
| 5. N⁴-Diethylaminomethylene-2'-deoxycytidine | $-N(C_2H_5)_2$ | 6.44 |
| 6. N⁴-Piperidinomethylene-2'-deoxycytidine | —N⟨ ⟩ (piperidino) | 7.79 |
| 7. N⁴-Diisopropylaminomethylene-2'-deoxycytidine | $-N[CH(CH_3)_2]_2$ | 15.79 |
| 8. N⁴-2,6-Dimethylpiperidinomethylene-2'-deoxycytidine | (2,6-dimethylpiperidino) | 21.81 |
| 9. N⁴-Di-n-butylaminomethylene-2'-deoxycytidine | $-N(nC_4H_9)_2$ | 125 |

EXAMPLE 3

Significant activity of N⁴-dimethylaminomethylene-2',3'-dideoxy-3'-fluorocytidine (DDFC, NSC D614989) and of N⁴-dimethylaminomethylene-2',3'-dideoxycytidine (DAM-ddC, NSC D621506) against human immunodeficiency virus (HIV-1, strain LAV) has been demonstrated by results obtained from the National Cancer Institute's In-Vitro Testing Program.

The protocol used in NCI's Developmental Therapeutics Program AIDS antiviral drug screening program involves plating of susceptible human "host" cells with and without virus in microculture plates, adding various concentrations of test material, incubating the plates for seven days (during which time infected, non-drug treated control cells are largely or totally destroyed by the virus), and then determining the number of remaining viable cells using a colorimetric endpoint. The dose dependent antiviral activity and cytotoxicity are determined and plotted on a graph. Two parameters can be extracted from the curves: the EC50, representing the concentration of drug that results in a 50% reduction of the viral cytopathic effect; and the IC50, representing the concentration of drug resulting in 50% cytotoxicity (growth inhibition derived from the normal, uninfected cultures). An in-vitro therapeutic index (TI) may be calculated as the ratio (IC50/EC50), if both values are obtained.

As shown by Figure in the anti-HIV drug screen of the National Cancer Institute, DDFC has shown significant antiviral activity in several cell lines. In the CEM cell line, complete protection against HIV was achieved by 8 micromolar DDFC without any cytotoxicity.

In all five different cell lines tested by NCI there was uniformly very little cytotoxicity observed with DDFC and the IC₅₀ could not be reached up to 200 μm, the highest concentration employed. These data are summarized in Table 2.

TABLE 2

Cytotoxicity of DDFC in the NCI in vitro anti-HIV drug screen

| CELL LINE | DATE OF TEST | IC₅₀, μM(μg/ml) |
|---|---|---|
| ATH8 | 9-08-87 | >200 (>56) |
| CEM | 1-13-88 | >200 (>56) |
| CEM | 1-23-88 | >0.2 (>0.055)[a] |
| CEM | 3-15-88 | >200 (>56) |
| CEM | 3-25-88 | >200 (>56) |
| CEM | 3-16-88 | >200 (>56) |
| C3-44 | 3-15-88 | >200 (>56) |
| C3-44 | 3-16-88 | >200 (>56) |
| LDV-7 | 3-15-88 | >200 (>56) |
| LDV-7 | 3-16-88 | >200 (>56) |
| LDV-7 | 3-25-88 | >200 (>56) |
| MT-2 | 1-29-88 | >200 (>56) |
| MT-2 | 3-25-88 | >200 (>56) |

[a] Highest concentration tested

Figure 2:
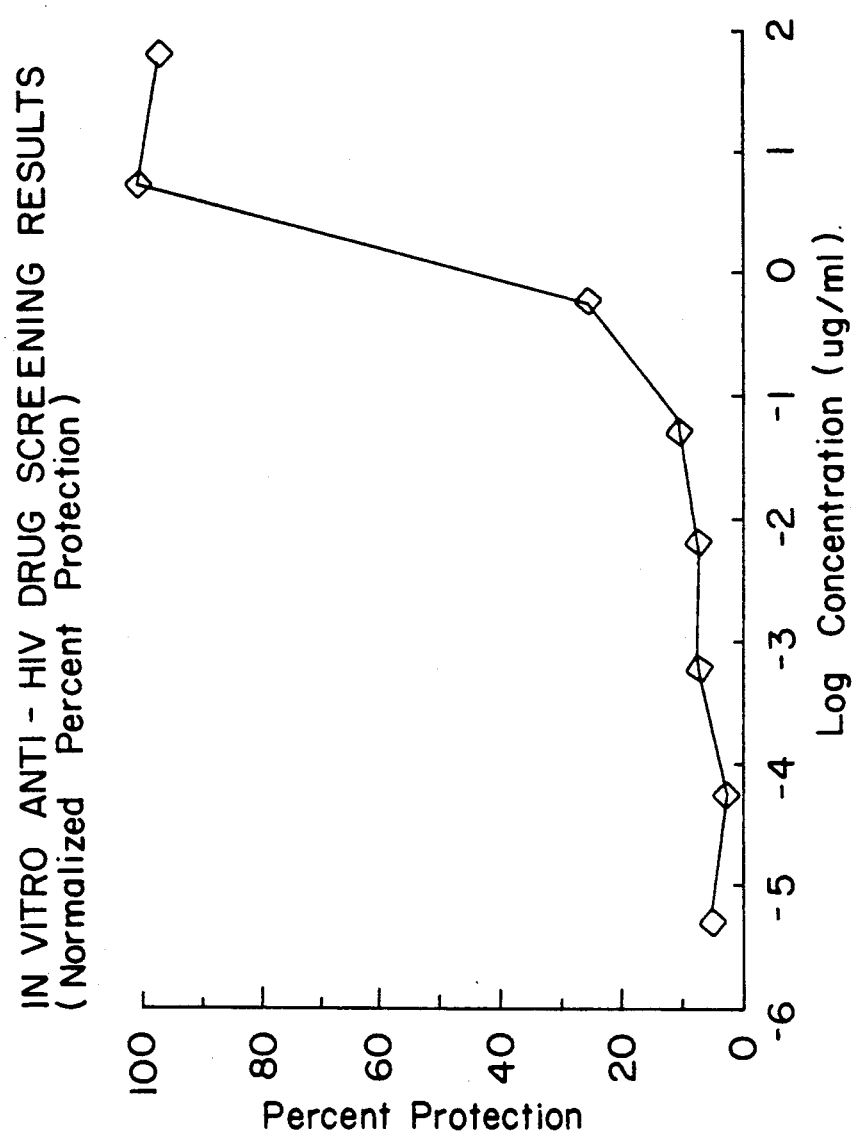

As shown in FIG. 2, the extent of protection of CEM cells by DDFC against the cytopathic effect of HIV correlated with the decrease in the presence of viral p24 antigen detected by enzyme-linked immunosorbent assay.

Figure 3:
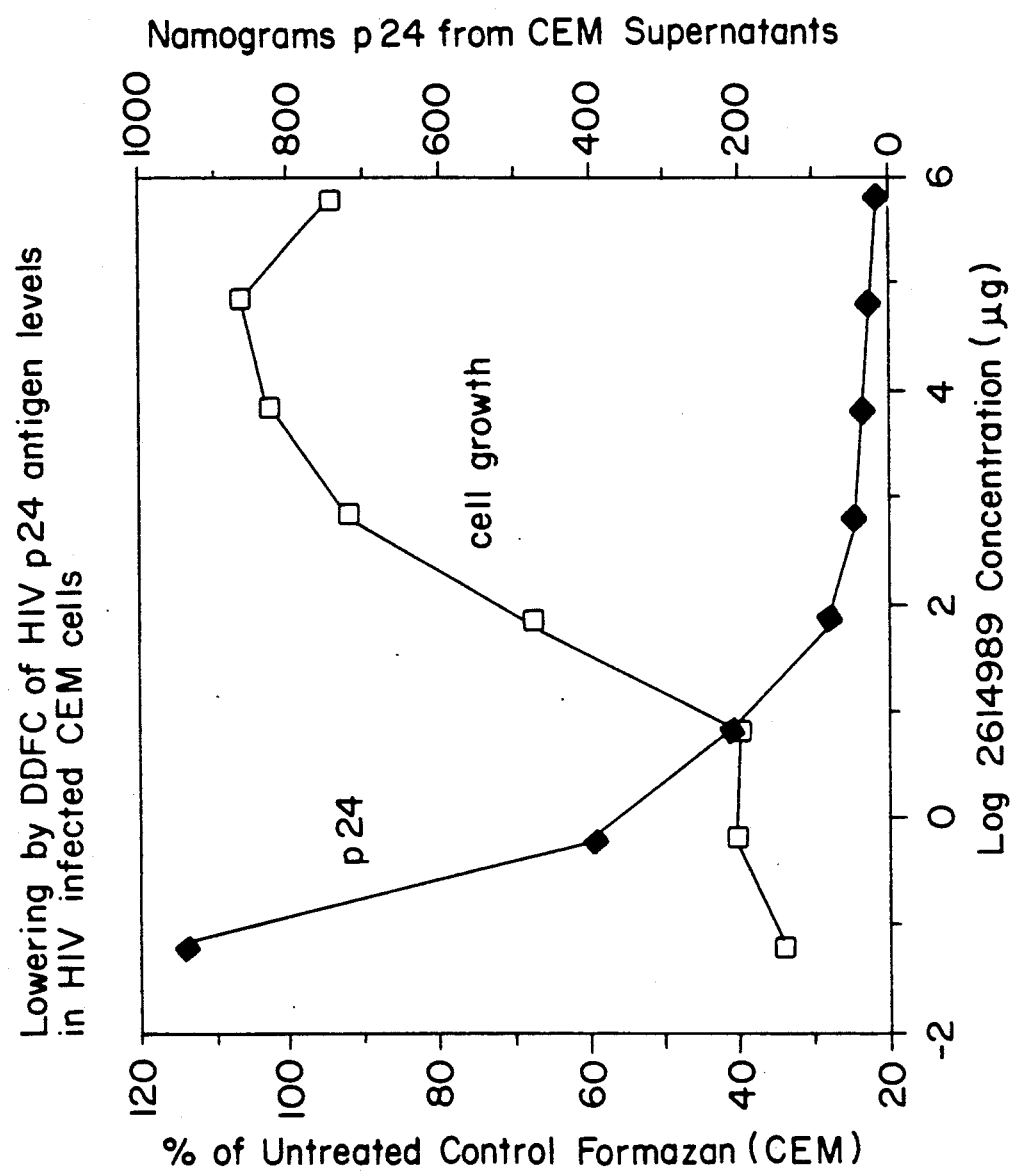

In the anti-HIV drug screen, N⁴-dimethylaminomethylene-2',3'-dideoxycytidine, likewise, showed significant antiviral activity as demonstrated in FIG. 3.

From the foregoing description, one skilled in the art to which this invention pertains, can easily ascertain the essential features thereof, and can make various changes and modifications to adapt it to various usages and conditions without departing from the spirit and scope thereof.

What is claimed is:

1. A compound of the formula

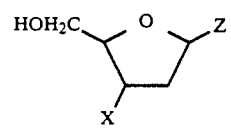

wherein X is hydrogen or fluorine and wherein Z is a pyrimidin-1-yl or a purin-9-yl base selected from the group consisting of cytosine, adenine and guanine, wherein divalently attached to the exocylic amino group on said base is a substituted methylene group having the formula

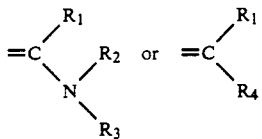

wherein $R_1$ is selected from the group consisting of hydrogen or a $C_1$-$C_{20}$ linear or branched chain alkyl, alkenyl, or alkynyl group and wherein $R_2$ and $R_3$ may be the same or different and each is selected from the group consisting of a $C_1$-$C_{20}$ linear or branched chain alkyl, alkenyl or alkynyl group or a $C_3$-$C_6$ cycloalkyl group or an aralkyl group and wherein $R_4$ is selected from the group consisting of pyrrolidines, piperidines or morpholines having the nitrogen divalently attached to the methylene group, and salts thereof.

2. The compound of claim 1 which is $N^4$-dimethylaminomethylene-2',3'-fluorocytidine.

3. The compound of claim 1 which is $N^4$-dimethylaminomethylene-2',3'-dideoxycytidine.

4. The compound $N^4$-diisopropylaminomethylene-2',3'-dideoxy-3'-fluorocytidine and salts thereof.

5. The compound of $N^4$-diisopropylaminomethylene-2',3'-dideoxycytidine and salts thereof.

6. The compound of claim 1 which is $N^6$-dimethylaminomethylene-2',3'-dideoxyadenosine.

7. The compound $N^6$-diisopropylaminomethylene-2',3'-dideoxyadenosine and salts thereof.

* * * * *